US008486406B2

(12) United States Patent
Burioni et al.

(10) Patent No.: US 8,486,406 B2
(45) Date of Patent: *Jul. 16, 2013

(54) MONOCLONAL ANTIBODIES AS A MEDICAMENT FOR THE THERAPEUTIC AND/OR PROPHYLACTIC TREATMENT OF SWINE-ORIGIN INFLUENZA A (H1N1) VIRUS (S-OIV) INFECTIONS

(75) Inventors: Roberto Burioni, Milan (IT); Massimo Clementi, Milan (IT)

(73) Assignee: Pomona Ricerca S.R.L., Turin (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/265,542

(22) PCT Filed: Jun. 1, 2010

(86) PCT No.: PCT/IB2010/052434
§ 371 (c)(1),
(2), (4) Date: Oct. 20, 2011

(87) PCT Pub. No.: WO2010/140114
PCT Pub. Date: Dec. 9, 2010

(65) Prior Publication Data
US 2012/0225068 A1 Sep. 6, 2012

(30) Foreign Application Priority Data
Jun. 1, 2009 (IT) .............. TO2009A0414

(51) Int. Cl.
A61K 39/395 (2006.01)
(52) U.S. Cl.
USPC ............. 424/147.1; 424/133.1; 424/135.1; 424/141.1
(58) Field of Classification Search
None
See application file for complete search history.

(56) References Cited

U.S. PATENT DOCUMENTS

| 4,946,778 | A | 8/1990 | Ladner et al. ........... 435/69.6 |
| 6,057,421 | A | 5/2000 | Muller et al. |
| 6,964,199 | B2 | 11/2005 | Lee et al. |
| 2003/0100741 | A1 | 5/2003 | Muller et al. |
| 2004/0224310 | A1 | 11/2004 | McGready |
| 2005/0080240 | A1 | 4/2005 | Kunert et al. |
| 2005/0221298 | A1 | 10/2005 | Muller et al. |

FOREIGN PATENT DOCUMENTS

| EP | 0621339 | 10/1994 |
| EP | 0675199 | 10/1995 |
| WO | 84/00687 | 3/1984 |
| WO | 92/15885 | 9/1992 |
| WO | 02/46235 | 6/2002 |
| WO | 02/055560 | 7/2002 |
| WO | 03/064473 | 8/2003 |
| WO | 2007/134327 | 11/2007 |
| WO | 2008/033159 | 3/2008 |
| WO | 2008/093280 | 8/2008 |
| WO | 2009/037297 | 3/2009 |
| WO | 2009/115972 | 9/2009 |
| WO | 2009/144667 | 12/2009 |
| WO | WO 2009144667 A1 * | 12/2009 |
| WO | 2010/073204 | 7/2010 |
| WO | 2010/140114 | 12/2010 |
| WO | WO 2011117848 A1 * | 9/2011 |

OTHER PUBLICATIONS

Burioni et al (Molecular cloning of the first human monoclonal antibodies neutralizing with high potency Swine-origin Influenza A pandemic virus (S-OIV), 2009, New Microbio, vol. 32 p. 319-324).*
Burioni et al (Molecular cloning of the First Human Monoclonal Antibodies Neutralizing with High Potency Swine-Origin Influenza A Pandemic Virus (S-OIV), New Microbio, 2009, vol. 32, p. 319-324).*
Padlan et al, Identification of Specificity-Determining Residues in Antibodies, 1995, FASEB J, vol. 9, p. 133-139.*
Webster (Webster's New World Medical Dictionary, 2003).*
Burton et al (Antibodies, viruses and vaccines, Nature, 2002, vol. 2, p. 706-713).*
Padlan et al (Identification of Specificity-determining residues in antibodies, 1995, FASEB, vol. 9, p. 133-139).*
Sui, Jianhua et al. "Structural and functional bases for broad-spectrum neutralization of avian and human influenza A viruses", Nature Structural and Molecular Biology, vol. 16, No. 3, pp. 265-273, Mar. 1, 2009.
Written Opinion for PCT/IB2010/052434 filed on Jun. 1, 2010, in the name of Pomona Biotechnologies LLC.
International Search Report for PCT/IB2010/052434 filed on Jun. 1, 2010, in the name of Pomona Biotechnologies LLC.
Ward, E.S. et al. "Binding activities of a repertoire of single immunoglobulin variable domains secreted from *Escherichia coli*", Nature, vol. 341, pp. 544-546, Oct. 12, 1989.
Burioni, R. et al. "Dissection of Human Humoral Immune Response Against Hepatitis C Virus E2 Glycoprotein by Repertoire Cloning and Generation of Recombinant Fab Fragments", Hepatology, vol. 28, No. 3, pp. 810-814, Sep. 1998.
Asanuma, H., et al., Influenza PR8 HA-specific fab fragments produced by phage display methods, *Biochemical and Biophysical Research Communication* 2008, 366: 445-449.
Austin, F., et al., Antigenic mapping of an Avian H1 Influenza virus haemagglutinin and interrelationships of H1virus from humans, pigs and birds, *Journal Gen. Virol.* 1986, 67: 983-992.
Baca, M., et al., Antibody Humanization Using Monovalent Phage Display, *Journal of Biological Chemistry* 1997, 272: 10678-10874.
Bansal, G. P., A summary of the workshop on passive immunization using monoclonal antibodies for HIV/AIDS, held at the National Institute of Allergy and Infectious Diseases, Bethesda, *Biol.* 2007, 35:367-371.
Barbas, C., et al., Human primers for fab amplification: Original set, *Phage Display Manual*, 2004, CSH Press, A1.6-A1.7.
Boudet, Florence et al. "Anti-Idiotypic Antibodies to the Third Variable Domain of gp120 Induce an Anti-HIV-1 Antibody Response in Mice," *Virology* 200, 176-188 (1994).

(Continued)

Primary Examiner — Sean E Aeder
Assistant Examiner — Julie Wu
(74) Attorney, Agent, or Firm — Steinfl & Bruno LLP

(57) ABSTRACT

The use of monoclonal antibodies Fab28 and Fab49 for the prophylactic or therapeutic treatment of swine-origin influenza A (H1N1) virus (S-OIV) infections is described, the which virus is responsible for the influenza syndrome commonly known as "swine flu". Moreover, the use of the above-mentioned antibodies for selecting potential vaccines for active immunization against S-OIV is described.

14 Claims, No Drawings

OTHER PUBLICATIONS

Braibant, M., et al. Antibodies to conserved epitopes of the HIV-1 envelope in sera from long-term non-progressors: prevalence and association with neutralizing activity, *AIDS*, 2006, 20: 1923-1930.

Bugli, F., et al., Mapping B-Cell Epitopes of Hepatitis C Virus E2 Glycoprotein Using Human Monoclonal Antibodies from Phage Display Libraries, *Journal of Virology*, Oct. 2001, 75: 9986-9990.

Burioni, R., et al., A Vector for the Expression of Recombinant Monoclonal Fab Fragments in Bacteria, *Journal of Immunological Methods* 1998, 217: 195-199.

Burton, Mouse primers for fab amplification: original set, *Phage Display Manual*, 2001, A1.10.

R. Burioni, "Nonneutralizing Human Antibody Fragment against Hepatitis C Virus E2 Glycoprotein Modulate Neutralization of Binding Activity of Human Recombinant Fabs", *Virology*, vol. 288; No. 1; 29-35 (2001).

Burioni, R., I Treponemi Intestinali Umani: Tesi per il conseguimento del dottorato di ricera in scienze microbiologiche di, 1993, 157, (Italian text with English abstract).

Carter, P., et al., Humanization of an Anti-p185her2 Antibody for Human Cancer Therapy, *PNAS* 1992, 89: 4285-4289.

Chen, C., et al., Enhancement and destruction of antibody function by somatic mutation: unequal occurence is controlled by V gene combinatorial associations, *EMBO J.* 1995, 14(12):2784-2794.

Cole, S., et al., A Strategy for the Production of Human Monoclonal Antibodies Reactive with Lung Tumor Cell Lines, *Cancer Research* 1984, 44: 2750-2753.

Eren et al., Preclinical Evaluation of Two Neutralizing Human Monocloncal Antibodies against Hepatitis C Virus (HCV): a Potential Treatment to Prevent HCV Reinfection in Liver Transplant Patients, *J. Virol.* 2006, vol. 80, pp. 2654-2664.

Final Office Action issued for U.S. Appl. No. 12/524,816, filed Jul. 28, 2009 in the name of Roberto Burioni, mail date: May 9, 2012.

Geretti AM, editor. De Luca, A., Antiretroviral Resistance in Clinical Practice. London: Mediscript; 2006, Chapter 12: The impact of resistance on viral fitness and its clinical implications.

Grant, Michael et al. "The anti-idiotypic antibody 1F7 selectively inhibits cytotoxic T cells activated in HIV-1 infection," *Immunology and Cell Biology*, 78, 20-27 (2000).

Gussow et al., Humanization of Monoclonal Antibodies, *Methods in Enzymology*, 1991, vol. 203, pp. 99-121.

Haigwood, N. L., Predictive value of primate models for AIDS, *AIDS Rev.* 2004, 6:187-198.

Hariharan, K., et al., Analysis of the cross-reactive Anti-gp120 antibody population in human immunodeficiency virus-infected asymptomatic individuals, *Journal of Virology*, 1993, 67: 953-960.

Holm et al., Functional mapping and single chain construction of the anti-cytokeratin 8 monoclonal antibody TS1, *Mol. Immunol.* Feb. 2007, vol. 44, No. 6, pp. 1075-1084.

Humbert, Michael et al. "Mimotopes selected with antibodies from HIV-1-neutralizing long-term nonprogressor plasma," *Eur. J. Immunol.* 2007, 37:501-515.

D. X. Johansson et al., "Human combinatorial libraries yield rare antibodies that broadly neutralize hepatitis C virus", *PNAS*, vol. 104; No. 41; 16269-16274 (2007).

Kasai, Yasushi et al. "Molecular cloning of murine monoclonal anti-idiotypic Fab," *Journal of Immunological Methods*, 155, 77-89 (1992).

Kunert, Renate et al. "Molecular Characterization of Five Neutralizing Anti-HIV Type 1 Antibodies: Identification of Nonconventional D Segments in the Human Monoclonal Antibodies 2G12 and 2F5," *AIDS Research and Human Retroviruses*, vol. 14, No. 13, pp. 1115-1128 (1998).

EISS, Low levels of influenza activity in Europe, EISS—*Weekly Electronic Bulletin*, Apr. 25, 2008.

MacCallum et al., Antibody-antigen Interactions: Contact Analysis and Binding Site Topography, *J. Mol. Biol.*, 1996, vol. 262, No. 5, pp. 732-745.

Mariuzza et al., The Structural Basis of Antigen-Antibody Recognition, *Annu. Rev. Biophys. Biophys. Chem.* 1987, vol. 16, pp. 139-159.

McMichael, J., HIV Vaccines, *Annual Review of Immunology*, Dec. 5, 2005, 24: 227-255.

Molinari, N., et al., The Annual Impact of Seasonal Influenza in the US: Measuring Disease Burden and Costs, *Vaccine* 2007, 25: 5086-5096.

Montefiori, D. C., Neutralizing antibodies take a swipe at HIV in vivo, *Nat. Med.* 2005, 11 (6):593-594.

Muller S. et al. "Generation and specificity of monoclonal anti-idiotypic antibodies against human HIV-specific antibodies," *Journal of Immunology*, vol. 147, No. 3, p. 933-941 (1991).

Muller, S. et al., Stimulation of Antiviral Antibody Response in SHIV-IIIB-Infected Macaques, *Scand. J. Immunol.* 2001, 45, pp. 383-395.

Muller S. et al. "Stimulation of HIV-1-neutralizing antibodies in simian HIV-IIIB-infected macaques," *Proc. Natl. Acad. Sci. USA*, vol. 95 pp. 276-281 (1998).

Nguyen, HH., et al., Heterosubtypic Immunity to Influenza A Virus Infection Requires B Cells but not CD8+ Cytotoxic T Lymphocytes, *The Journal of Infectious Diseases* 2001, 183: 368-376.

"NIH AIDS Research and Reference Reagent Program, About the Program" https://www.aidsreagent.org/about_program.cfm, n.d.; n.p.; retrieved from web. Jan. 23, 2012.

"NIH AIDS Research & Reference Reagent Program, Reagent Information, U87.CD4", https://www.aidsreagent.org/reagentdetail.cfm?t=cell_lines&id=20; Jun. 15, 2011, n.p.; retrieved from web. Jan. 23, 2012.

Non-Final Office Action issued for U.S. Appl. No. 12/524,816, filed Jul. 28, 2009 in the name of Roberto Burioni et al. mail date: Jul. 21, 2011.

Non-Final Office Action issued for U.S. Appl. No. 13/141,071, filed Jun. 20, 2011 in the name of Roberto Burioni et al.; mail date: Mar. 9, 2012.

Oxford University Press, *Virus Culture—A Practical Approach*, ed. A.J. Cann, 2000, p. 84.

Pantophlet, et al., "GP120: Target for Neutralizing HIV-1 Antibodies", *Annual Review Immunology* 2006, 24: 739-769.

PCT International Search Report issued for PCT Application No. PCT/IB2008/050307 filed on Jan. 29, 2008 in the name of Pomona Biotechnologies Inc.

PCT International Preliminary Report on Patentability issued for PCT Application No. PCT/IB2008/050307 filed on Jan. 29, 2008 in the name of Pomona Biotechnologies Inc.

PCT Written Opinion issued for PCT Application No. PCT/IB2008/050307 filed on Jan. 29, 2008 in the name of Pomona Biotechnologies Inc.

PCT International Search Report issued for PCT Application No. PCT/IB2009/052212 filed on May 27, 2009 in the name of Pomona Biotechnologies Inc.

PCT Written Opinion issued for PCT Application No. PCT/IB2009/052212 filed on May 27, 2009 in the name of Pomona Biotechnologies Inc.

PCT International Search Report issued for PCT Application No. PCT/IB2009/051068 filed on Mar. 16, 2009 in the name of Pomona Biotechnologies Inc.

PCT Written Opinion issued for PCT Application No. PCT/IB2009/051068 filed on Mar. 16, 2009 in the name of Pomona Biotechnologies Inc.

PCT International Search Report for PCT/IB2009/055867 filed Dec. 21, 2009 in the name of Bait Biotecnologie Applicate Italiane S.R.L.

PCT Written Opinion for PCT/IB2009/055867 filed Dec. 21, 2009 in the name of Bait Biotecnologie Applicate Italiane S.R.L.

PCT International Search Report for PCT/IT2003/000032 (WO 03/064473) filed Jan. 29, 2003 in the name of Roberto Burioni.

PCT International Search Report for PCT/US2001/045221 (WO 02/055560) filed Nov. 30, 2001 in the name of The Gouvernment of the United States of America, as represented by the Secretary Department of Health and Human Services.

PCT Search Report for International Application PCT/IB2010/052434 filed on Jun. 1, 2010 in the name of Pomona Ricerca S.R.L.

PCT Written Opinion for International Application PCT/IB2010/052434 filed on Jun. 1, 2010 in the name of Pomona Ricerca S.R.L.

Perotti, M., et al., Identification of a broadly cross-reacting and neutralizing human monoclonal antibody directed against the Hepatitis C virus E2 protein, *Journal of Virology* 2008, 82: 1047-1052.

Rangel-Moreno, J., et al., B Cells Promote Resistance to Heterosubtypic Strains of Influenza via Multiple Mechanisms, *The Journal of Immunology* 2008, 180: 454-463.

Restriction Requirement issued for U.S. Appl. No. 12/524,816, filed Jul. 28, 2009 in the name of Roberto Burioni et al. mail date: Apr. 5, 2011.

Restriction Requirement issued for U.S. Appl. No. 13/141,071, filed Jun. 20, 2011 in the name of Roberto Burioni et al.; mailing date: Nov. 14, 2011.

Rudikoff et al., Single amino acid substitution altering antigen-binding specificity, *Proc. Natl. Acad. Sci. USA*, 1982, vol. 79, pp. 1979-1983.

Smirnov, Y. et al., "An epitope shared by the hemagglutinins of H1, H2, H5, and H6 subtypes of influenza A virus." *Acta Virologica* 43(4):237-244 (1999).

Smirnov, Y. et al., "Prevention and treatment of bronchopneumonia in mice caused by mouse-adapted variant of avian H5N2 influenza A virus using a monoclonal antibody against conserved epitope in the HA stem region." *Archives of Virology* 145(8):1733-1741 (2000).

Stamatatos, L. et al., Neutralizing antibodies generated during natural HIV-1 infection: good news for an HIV-1 vaccine? *Nature Medicine*, Aug. 2009, vol. 15, No. 8, pp. 866-870.

Staprans, S. I., and M. B. Feinberg, The roles of nonhuman primates in the clinical evaluation of candidate AIDS vaccines, *Exp. Rev. Vacc.* 2004, 3(4):S5-S32.

A. Tarr et al., "Characterization of the Hepatitis C Virus E2 Epitope Defined by the Broadly Neutralizing Monoclonal Antibody AP33", *Hepatology*, vol. 43; No. 3; 592-601 (2006).

Tarr, A.W. et al., "Determination of the human antibody response to the epitope defined by the hepatitis C virus-neutralizing monoclonal antibody AP33", *Journal of General Virology* 2007, 88, 2991-3001.

Thompson, W., et al., Mortality Associated with Influenza and Respiratory Syncytial Virus in the United States, *JAMA* 2003, 289: 179-186.

Throsby, M. et al., "Heterosubtypic neutralizing monoclonal antibodies cross-protective against H5N1 and H1N1 recovered from human IgM+ memory B cells." *PLOS ONE* 3(12):1-15 (2008).

Tkacova, M., et al., Evaluation of monoclonal antibodies for subtyping of currently circulating human type A viruses, *Journal of Clinical Microbiology* 1997, 35: 1196-1198.

Trkola, A., et al., Delay of HIV-1 rebound after cessation of antiretroviral therapy through passive transfer of human neutralizing antibodies, *Nat. Med.* 2005, 11 (6):615-622.

UNAIDS—AIDS Epidemic Update: Special Report on HIV Prevention—Dec. 2005.

Wang, Haitao et al. "Human monoclonal and polyclonal anti-human immunodeficiency virus-1 antibodies share a common clonotypic specificity," *Eur. J. Immunol.* 1992, 22:1749-1755 (1992).

Wang, Q.L. et al. "Identification of an Idiotypic Peptide Recognized by Autoantibodies in Human Immunodeficiency Virus-1-infected Individuals," *J. Clin. Invest.* vol. 96, 775-780 (1995).

Winkler, K., et al., Changing the antigen binding specificity by single point mutations of an anti-p24 (HIV-1) antibody, *J. Immunol.* 2000, 165:4505-4514.

Ziegler, T. et al., "Type- and subtype-specific detection of influenza viruses in clinical specimens by rapid culture assay." *Journal of Clinical Microbiology* 33(2):318-321 (1995).

\* cited by examiner

MONOCLONAL ANTIBODIES AS A MEDICAMENT FOR THE THERAPEUTIC AND/OR PROPHYLACTIC TREATMENT OF SWINE-ORIGIN INFLUENZA A (H1N1) VIRUS (S-OIV) INFECTIONS

CROSS REFERENCE TO RELATED APPLICATIONS

The present application is the US national stage of International Application PCT/IB2010/052434 filed on Jun. 1, 2010, which in turn, claims priority to Italian Patent Application TO2009A000414 filed on Jun. 1, 2009. The present application may also be related to International Application PCT/IB2009/055867 filed on Dec. 21, 2009 and its related U.S. national phase Ser. No. 13/141,071 filed on Jun. 20, 2011, International Application PCT/IB2009/052212 filed on May 27, 2009 and its related U.S. national phase Ser. No. 12/994,746 filed on Nov. 24, 2010, International Application PCT/IB2008/050307 filed on Jan. 29, 2008 and its related U.S. national phase Ser. No. 12/524,816 filed on Jul. 28, 2009 and to International Application PCT/IB2009/051068 filed on Mar. 16, 2009 and its related U.S. national phase Ser. No. 12/922,850 filed on Sep. 15, 2010.

The present invention in general falls within the field of immunology. More specifically, the invention concerns the use of monoclonal antibodies for the therapeutic and/or prophylactic treatment of swine-origin influenza A (H1N1) virus (S-OIV) infections, commonly known as the "swine influenza virus".

The appearance of novel isolates is a constant event in the epidemiological interaction between influenza viruses and mankind. Cyclically, the new emerging variants acquire the ability of eluding the previously existing immune responses induced by circulating strains. If these new variants gain the ability of being transmitted from man to man, the risk of a worldwide epidemic (pandemic) becomes real. The appearance of pandemic strains is a consequence of the genomic organization of influenza viruses, characterized by the presence of eight distinct single-stranded RNA segments. These completely new influenza viruses usually originate from a genetic rearrangement of RNA fragments from different animal and human viruses in an animal host, generally a pig.

This could be the mechanism that in 1918 gave rise to the pandemic strain of the so-called "Spanish flu" (even though the molecular details are not completely clarified), which according to estimates caused the death of approximately 100 million people.

Recently the 1918 virus has been reconstructed in the laboratory by applying molecular biology techniques and has shown the ability of infecting swine. Researchers postulate that this originally-avian virus has acquired the ability of infecting swine in the course of the pandemic. It is not clear whether it has infected human beings through direct transmission from birds (usually avian viruses do not replicate well in human beings) or if this has happened by means of a previous adaptation in the pig.

Something similar also happened with a milder pandemic virus, the H2N2 strain accountable for the so-called Asian flu in 1957. In particular, three H2N2 avian virus genes inserted themselves into the H1N1 human strain giving rise to a new virus capable of causing a pandemic. Here also, the recombination probably occurred in the pig.

A very similar phenomenon has been recently observed with the emergence of a swine-origin influenza A (H1N1) virus (S-OIV), first identified in Mexico in April 2009, which, according to the data available up to May 18, 2009, has affected 8829 patients in 40 countries and caused 74 deaths. Since the first isolation of the virus S-OIV, it was immediately evident that transmission between human beings is the factor that allows this virus to spread. From the genetic point of view, this virus contains a combination of gene segments never described before, neither in swine nor in human beings. Two fragments (fragment #6 encoding for neuraminidase and fragment #7 encoding for M proteins) are swine genes originally derived from an avian influenza virus and first detected in swine in 1979; three fragments (fragment #4 encoding for hemagglutinin, fragment #5 encoding for the nucleoprotein and fragment #8 encoding for non-structural proteins) are classical swine genes circulating in the pig since 1918; three fragments (fragments #1, #2 and #3 encoding for the components of the viral RNA polymerase) derive from the so-called triple swine reassortment, a strain circulating in pigs since 1998 which derives from a swine-avian-human rearrangement.

From the antigen point of view, S-OIV is very distant from the H1N1 human isolates now circulating. Actually, serum samples from ferrets immunized with the now-circulating human viruses do not react with S-OIV, which demonstrates the distance existing between the two strains. Nevertheless the possibility, at least to a certain extent, of a cross-protection induced by the preexisting H1N1 antibody response can not be ruled out a priori, as it has already been found that immunization with a given strain can stimulate memory B lymphocytes against viruses that are temporally distant but genetically related.

Many epidemiological data seem to point in this direction, as a higher mortality rate has been observed in patients under 65 years of age, which points out a possible protective role played in older patients by the antibodies directed against H1N1 viruses that circulated in the fifties or even before that.

This information is extremely precious with regard to the prophylactic and therapeutic aspects. The main problem in this acute phase of the epidemic is that S-OIV resulted to be only partially sensitive to neuraminidase inhibitors (oseltamivir and zanamivir), being otherwise resistant to inhibitors of M2 ion channels (amantadine and rimantadine).

As usual, a vaccine approach requires a lot of time and, furthermore, it is not clear which virus isolates should be included in the vaccine. In particular, the safety problems related to the use of a completely new and potentially pandemic virus can not be ignored. Other approaches, such as passive immunization with neutralizing antibodies, must thus be taken into due consideration.

Therefore, there is a tremendous need of rapidly identifying antibodies that are effectively capable of binding to and neutralizing the swine-origin influenza A (H1N1) virus (S-OIV) and are thus suitable for use as a medicament to fight or prevent S-OIV infections and, more generally, to fight or prevent any pathology related to this new virus, such as the influenza syndrome commonly known as the "swine flu".

Such a need has been met by the present inventors who proved that two Fab fragments of human monoclonal antibodies designated as Fab28 and Fab49, described in the Italian Patent Applications TO2008A000204 of Mar. 17, 2008, and TO2008A000398 of May 27, 2008, respectively, are able to effectively bind to and neutralize the swine-origin influenza A (H1N1) virus (S-OIV).

Monoclonal antibodies Fab28 and Fab49 are defined by the nucleotide and amino acid sequences of the variable regions of their light and heavy chains.

The amino acid sequence of the heavy chain variable region of Fab28 is designated as SEQ ID NO:1 in the Sequence Listing.

The amino acid sequence of the light chain variable region of Fab28 is designated as SEQ ID NO:2 in the Sequence Listing.

The nucleotide sequence of the heavy chain variable region of Fab28 is designated as SEQ ID NO:3 in the Sequence Listing.

The nucleotide sequence of the light chain variable region of Fab28 is designated as SEQ ID NO:4 in the Sequence Listing.

The amino acid sequence of the heavy chain variable region of Fab49 is designated as SEQ ID NO:5 in the Sequence Listing.

The amino acid sequence of the light chain variable region of Fab49 is designated as SEQ ID NO:6 in the Sequence Listing.

The nucleotide sequence of the heavy chain variable region of Fab49 is designated as SEQ ID NO:7 in the Sequence Listing.

The nucleotide sequence of the light chain variable region of Fab49 is designated as SEQ ID NO:8 in the Sequence Listing.

The data achieved by the inventors, described in detail in the experimental section of the present description, suggest that the antibodies Fab28 and Fab49 are extremely effective in conferring a passive immunity towards S-OIV to the subjects to whom they are administered and accordingly are effective in the prophylactic or therapeutic treatment of S-OIV infections and the caused pathologies related therewith, such as for example the influenza syndrome commonly known as the "swine flu".

Such a result was totally unexpected since till now, as far as the inventors know, no monoclonal antibody had been identified which was able to effectively bind to and neutralize a swine-origin influenza A (H1N1) virus (S-OIV) isolate.

Thus, a first aspect of the invention is the monoclonal antibody Fab28 or the monoclonal antibody Fab49 as a medicament for the prophylactic or therapeutic treatment of swine-origin influenza A (H1N1) virus (S-OIV) infections or any pathology related therewith, such as the so-called "swine flu".

The attainment of the human monoclonal antibodies Fab28 and Fab49 and their binding properties are described in detail in the experimental sections of the Italian Patent Applications TO2008A000204 of Mar. 17, 2008, and TO2008A000398 of May 27, 2008, respectively.

Given that the amino acid and nucleotide sequences of the variable domains of their heavy and light chains are known, it is possible to manufacture the antibodies Fab28 and Fab49 by the usual recombinant DNA methods widely known to the person of average skill in the art.

In particular, the experimental section of the above-identified Italian Patent Applications describes the preparation of the monoclonal antibodies Fab28 and Fab49 in the form of Fab fragments. It is however to be understood that the monoclonal antibodies Fab28 and Fab49 may also be prepared and used under other forms, such as for example whole immunoglobulins, or in the form of other antibody fragment types, such as for example F(ab')$_2$ fragments or antibody fragments smaller than Fabs, or even as peptides having the same immunological properties as those experimentally demonstrated for the Fabs.

Single chain antibodies for instance are constructed according to the method described in U.S. Pat. No. 4,946,778 by Ladner et al. Single chain antibodies comprise the light and heavy chain variable regions linked by a flexible linker. The antibody fragment designated as single domain antibody is even smaller than the single chain antibody, as it comprises only one isolated VH domain. Techniques for obtaining single domain antibodies having, at least partially, the same binding ability as the whole antibody, are described in the prior art and fall within the knowledge of the person of average skill in the art. Ward, et al., in "Binding Activities of a Repertoire of Single Immunoglobulin Variable Domains Secreted from *Escheria coli*," Nature 341:544-546, describes a screening method for obtaining the variable region of an antibody's heavy chain (VH single domain antibody) with a sufficient affinity for the target epitope to bind to it in an isolated form.

In the description that follows, the term "antibody" is thus used to refer to any form into which an antibody can be manufactured and used, for instance whole immunoglobulins, Fab fragments or other antibody fragment types, single chain antibodies, single domain antibodies, etc.

The monoclonal antibodies used in the invention can be manufactured and used in a free form or in a carrier-conjugated form. A carrier is a molecule or chemical or biological entity capable of conjugating with an antibody and making it immunogenic or increasing its immunogenicity. Non-limiting examples of carriers are proteins such as KLH (keyhole limpet hemocyanin), edestin, thyroglobulin, albumins as bovine serum albumin (BSA) or human serum albumin (HSA), erythrocytes such as sheep erythrocytes (SRBC), tetanus anatoxin, cholera anatoxin, poly-amino acids such as for example poly(D-lysine:D-glutamic acid) and, the like. In order to facilitate the binding of the antibody to the carrier, the antibody C-terminus or N-terminus may be modified, for example, by the insertion of additional amino acid residues, for instance one or more cysteine residues that are able to form disulfide bridges.

Given their neutralizing properties, the monoclonal antibodies Fab28 and Fab49 are suitable for use in the manufacture of a medicament for the prophylactic or therapeutic treatment of swine-origin influenza A (H1N1) virus (S-OIV) infections.

Thus, the use of Fab28 antibody or Fab49 antibody for the manufacture of a medicament for the prophylactic or therapeutic treatment of infections caused by swine-origin influenza A (H1N1) virus (S-OIV) infections or any pathology related therewith, such as the so-called "swine flu", is within the scope of the invention.

In this context too, the expression "Fab28 antibody or Fab49 antibody" includes not only the Fab fragments of the above-identified monoclonals, but also any other form into which such monoclonals may be prepared and used, for example whole immunoglobulins, other kinds of antibody fragments, single chain antibodies, etc.

Furthermore, the monoclonal antibodies Fab28 and Fab49 are suitable for use as assay reagents for selecting a candidate vaccine for the active immunization against the swine-origin influenza A (H1N1) virus (S-OIV). In fact, if the vaccine binds the antibody Fab28 and/or the antibody Fab49, it is conceivable that the vaccine itself contains the epitope or epitopes recognized by, the antibody Fab28 and/or the antibody Fab49 and thus is able to induce at least one of such antibodies in the subject to which it is administered.

In general, the antibodies Fab28 and/or Fab49 in the form of whole immunoglobulins or antibody fragments as defined above are suitable as assay reagents for selecting a vaccine for the active immunization against S-OIV, as is also any linker containing the antibody Fab28 and/or Fab49, or a portion thereof, and having the same binding properties as the antibody Fab28 and/or Fab49.

In this context, a vaccine is a preparation containing material consisting of whole killed or attenuated S-OIV virus, or consisting of fragments of the virus, such as for example one or more S-OIV virus antigens, or single virus proteins in a native or modified form, expressed in any eukaryotic and/or prokaryotic expression system.

Another aspect of the invention is thus an assay method for selecting a vaccine effective for the active immunization against the swine-origin influenza A (H1N1) virus (S-OIV), comprising the steps of:

(a) contacting a candidate vaccine for the active immunization against the swine-origin influenza A (H1N1) virus (S-OIV) with at least one linker comprising the antibody Fab28 and/or the antibody Fab49 or comprising at least a linking portion of the antibody Fab28 and/or of the antibody Fab49, such that said linker has substantially the same binding ability to the swine-origin influenza A (H1N1) virus (S-OIV) as the antibody Fab28 and/or the antibody Fab49;

(b) detecting whether a binding between the candidate vaccine and the above-mentioned at least one linker occurs, the binding being indicative of the effectiveness of the vaccine.

Such a method is useful for the assessment of any preparation to be used as a vaccine or immunogenic preparation.

The ability of the monoclonal antibodies Fab28 and Fab49 to react with cells infected by the swine-origin influenza A (H1N1) virus (S-OIV) is proved in the experimental section that follows. To this end, immunofluorescence assays were carried out. In addition, a neutralizing assay was performed in order to demonstrate the in vitro biological activity of the antibodies Fab28 and Fab49. In this assay, the antibodies Fab28 and Fab49 showed an effective neutralizing activity towards a swine-origin influenza A (H1N1) virus (S-OIV) isolate obtained by the inventors from an infected subject from the United States with clinical symptoms suggesting an S-OIV infection.

The partial nucleotide sequence (SEQ ID NO:9) and the partial amino acid sequence (SEQ ID NO:10) of the hemagglutinin gene from this new S-OIV isolate, designated as A/Milano/UHSR1/2009 (H1N1), are provided in the Sequence Listing.

The following experimental section is provided solely by way of illustration and not limitation of the scope of the invention, as defined in the appended claims. The claims are an integral part of the present disclosure.

EXPERIMENTAL SECTION

Virus Isolation, Identification and Cultivation

A cell line designated as MDCK (Madin-Darby canine kidney) (ATCC® no. CCL-34TM) propagated in Modified Eagle Medium (MEM) (GIBCO), supplemented with 10% inactivated (treatment at 56° C. for 30 minutes) fetal bovine serum (FBS) (EuroClone), 50 µg/ml penicillin, 100 µg/ml streptomycin (GIBCO) and 2 mM L-glutamine (EuroClone) was used for isolating the S-OIV virus. The cells were incubated at 37° C. in a 5% $CO_2$ atmosphere and were passaged at a 1:3 ratio twice a week. The virus was isolated from a nasopharyngeal swab of an infected patient with a recent history of a trip to the United States and symptoms suggesting an S-OIV infection, by seeding it on confluent MDCK cells in MEM medium, supplemented with 1 µg/ml serum-free trypsin (SIGMA). Identification occurred by polymerase chain reaction amplification preceded by reverse transcription of a viral hemagglutinin region, sequencing thereof and comparison with the sequences filed in public databases (www.ncbi.nlm.nih.gov). The amplification and sequencing procedure was carried out both on the patient's sample and on the cell culture, with identical results.

The amplification was performed by using the following primer pair: Bm-NS-890-Rev ATATCGTCTCGTATTAGTA-GAAACAAGGGTGTTT (SEQ ID NO: 11) and Bm-HA-1-Fw TATTCGTCTCAGGGAGCAAAAGCAGGGG (SEQ ID NO:12). The reaction was carried out by using Taq Platinum (Invitrogen) using the following temperature profile: 10 min 94° C., 40 cycles: 94° 30", 53° 1', 72° 1'. The sequencing was performed by using the primers that follow: H1-F1 CTTAGGAAACCCAGAATGCG (SEQ ID NO:13), H1-F2 TACTGGACCTTGCTAGAACC (SEQ ID NO:14), H1-F3 GGTCTATTTGGAGCCATTGC (SEQ ID NO:15). The sequencing reaction was carried out by using the BigDye Terminators 3.1 chemistry and the automated sequencer Abi-Prism3130 (Applied Biosystems). The sequence resulted to be >98% identical to the sequence from the S-OIV isolate considered as the reference A/Mexico/4575/2009 (H1N1) accountable for the swine flu pandemic, which confirmed that the isolated strain is an S-OIV. The S-OIV strain isolated from the patient in question was designated as A/Milano/UHSR1/2009 (H1N1).

The virus stocks were obtained from the culture supernatant as extracellular viruses. Generally 4 days after the infection the supernatant was collected, centrifuged at 1000 RCF (relative centrifugal force) for 10 minutes to eliminate the cell debris and filtered with 0.22 µm filters (MILLIPORE). The supernatant was then aliquoted and stored at −80° C. as cell-free viruses.

Immunofluorescence Assessment of Fab49 and Fab28

Fab49 and Fab28 were assessed by an immunofluorescence assay. Briefly, the cells from the cultures infected with the S-OIV virus were trypsinized and, after two washes in PBS, counted under a microscope with a hematocytometer. The cell suspension was thus used for the preparation of slides by centrifugation in a cytocentrifuge (Cytospin4, Shandon Southern Products) at 90 g for 3 minutes. The so prepared slides each contained a total of $2 \times 10^5$ cells. Control slides were prepared similarly with uninfected cells. The cells were then fixed and permeabilized at room temperature with a methanol-acetone solution (used at the temperature of −20° C.) for 10 minutes. After 3 washes in PBS, the cells were incubated with Fab49 or Fab28 (100 µg/ml) for 30 minutes at 37° C. in a humid chamber and subsequently washed three times in PBS. The cells were then incubated for 30 minutes at 37° C. in the humid chamber in the dark with a fluorescein isothiocyanate-conjugated goat Fab (Sigma) diluted 1:200 in Evans Blue. The slides were examined under a fluorescence microscope (Olympus). A commercial mouse monoclonal (Argene) specific for the NP influenza virus protein was used as a positive control. An antibody directed against the E2 glycoprotein of the hepatitis C virus (e509; Burioni et al, Hepatology, 1998) was used as a negative control. By immunofluorescence, Fab49 and Fab28 showed a specific reactivity for all the cells infected with the A/Milano/UHSR1/2009 (H1N1) isolate. The fluorescence pattern displayed was clearly a cytoplasm-type pattern. Instead, no fluorescence was seen in uninfected cells, cells infected with a reference isolate from the B-type influenza virus, or with the negative control antibody.

Neutralization Assay

In order to characterize the in vitro biological activity of Fab28 and Fab49, a neutralization assay was designed for the A/Milano/UHSR1/2009(H1N1) isolate. In short, MDCK cells were seeded into MEM-10% FBS in a 96-well plate ($2 \times 10^4$ cells/well). Serial dilutions (from $10^{-1}$ to $10^{-8}$) of the virus stocks, obtained as described above, were prepared in maintenance medium (MEM with 2% FBS). Each dilution was repeated six times. When the cultured cells were confluent, the growth medium was removed and 100 μl of each of the virus dilutions were added to each well. After 1 hour at 37° C., the inocula were removed and 200 μl of MEM medium added with 1 μg/ml trypsin were placed into each well. The viral titer, expressed as $TCID_{50}$ (the dose that infects 50% of the cell culture), was calculated by applying Reed-Muench's formula:

$$TCID_{50} = \frac{\text{infectivity} > 50\% - 50\%}{\text{infectivity} > 50\% - \text{infectivity} < 50\%} \times \text{dilution factor}$$

In the light of the obtained data, the virus stock was diluted so as to use a multiplicity of infection (M.O.I.) of approximately 0.01 (1 virus particle per 100 cells) in the neutralization experiment. In the actual neutralization assay, the cells were seeded in a 24-well plate, with each well containing a sterile slide. The neutralization experiment was performed on 80%-90% confluent cells, i.e. about 48 hours after the seeding thereof. Dilutions of the purified Fab49 or Fab28 were then prepared, so as to attain final concentrations of 1 μg/ml, 5 μg/ml, 10 μg/ml and 20 μg/ml. Corresponding dilutions of the e509 anti-HCV antibody were prepared as a negative control. The various Fab concentrations were then incubated with the same volume of diluted virus stock (M.O.I.: 0.01) for 1 hour at 37° C. 250 μl of the virus-Fab mix were subsequently added to the wells containing the cells. A positive control for the infection was achieved by adding the culture medium alone to the virus stock. The plate was incubated for 1 hour at 37° C. in order to allow the non-neutralized virus to adsorb. The inoculum was then removed and the cells were washed twice with PBS. 1.5 ml of serum-free medium with 1 μg/ml trypsin were added to each well. After a 6-hour incubation at 37° C., the cell monolayer was washed with PBS and fixed with a cold methanol-acetone solution (1:2 ratio, stored at −20° C.) for 10 minutes at room temperature. The fixed cells were washed and incubated with 250 μl of a commercial monoclonal anti-NP antibody (Argene) for 30 minutes at 37° C. in a humid chamber. The cells were washed with PBS and finally incubated with a fluorescein-conjugated goat anti-mouse antibody and diluted in Evans blue for 30 minutes at 37° C. in a humid chamber in the dark. After three washes in PBS, the slides were finally examined under a fluorescence microscope. The neutralizing activity of Fab49 and Fab28 was determined by counting the single positive cells and calculating the percentage decrease in the number of infected cells, compared to the positive control infected with the virus alone. The neutralization assays were carried out in three separate sessions for each of the isolates used for the neutralization assays. In each experiment, the different Fab49 dilutions were repeated in triplicate, similarly to what performed for the negative (Fab e509 anti-E2/HCV) and positive (virus and Fab-free medium) controls of infection. The experiments performed showed that the antibodies Fab 28 and Fab 49 are able to neutralize the S-OIV A/Milano/UHSR1/2009 isolate at extremely low concentrations, with an IC50 of 2 μg/ml.

The invention claimed is:

1. A medicament comprising an engineered monoclonal antibody, wherein the monoclonal antibody comprises one heavy chain variable domain and one light chain variable domain, the heavy chain variable domain consisting of the amino acid sequence SEQ ID NO:5 or being fully encoded by the nucleic acid sequence SEQ ID NO:7 and the light chain variable domain consisting of the amino acid sequence SEQ ID NO:6 or being fully encoded by the nucleic acid sequence SEQ ID NO:8, and wherein the medicament is for the therapeutic treatment of swine-origin influenza A (H1N1) virus (S-OIV) infections.

2. A method for therapeutic treatment of swine-origin influenza A (H1N1) virus (S-OIV) infection in a patient, the method comprising administering to said patient an engineered monoclonal antibody wherein the monoclonal antibody comprises one heavy chain variable domain and one light chain variable domain, the heavy chain variable domain consisting of the amino acid sequence SEQ ID NO:5 or being fully encoded by the nucleic acid sequence SEQ ID NO:7 and the light chain variable domain consisting of the amino acid sequence SEQ ID NO:6 or being fully encoded by the nucleic acid sequence SEQ ID NO:8.

3. The method according to claim 2, wherein the monoclonal antibody is selected from the group consisting of whole immunoglobulins and immunoglobulin fragments comprising at least one heavy chain variable domain and one light chain variable domain.

4. The method according to claim 3, wherein said immunoglobulin fragments are selected from the group consisting of Fab fragments, Fab' fragments, $F(ab')_2$ fragments, Fv fragments and single chain antibodies (scFv).

5. The method according to claim 4, wherein the monoclonal antibody is a human antibody.

6. The medicament according to claim 1, wherein the monoclonal antibody is selected from the group consisting of whole immunoglobulins and immunoglobulin fragments, the immunoglobulin fragments comprising at least one heavy chain variable domain and at least one light chain variable domain.

7. The medicament according to claim 6, wherein said immunoglobulin fragments are selected from the group consisting of Fab fragments, Fab' fragments, $F(ab')_2$ fragments, Fv fragments, single chain antibodies (scFv).

8. The medicament according to claim 1, wherein the antibody is a human antibody.

9. A method for preparing a medicament according to claim 1, the method comprising:

preparing a monoclonal antibody suitable for the therapeutic treatment of swine-origin influenza A (H1N1) virus (S-OIV) infections, wherein the antibody comprises one heavy chain variable domain consisting of the amino acid sequence SEQ ID NO:5 or fully encoded by the nucleic acid sequence SEQ ID NO:7 and one light chain variable domain consisting of the amino acid sequence SEQ ID NO:6 or being fully encoded by the nucleic acid sequence SEQ ID NO:8.

10. A medicament comprising an engineered monoclonal antibody, wherein the monoclonal antibody comprises one heavy chain variable domain and one light chain variable domain, the heavy chain variable domain consisting of the amino acid sequence SEQ ID NO: 5 or being fully encoded by the nucleic acid sequence SEQ ID NO: 7 and the light chain variable domain consisting of the amino acid sequence SEQ ID NO: 6 or being fully encoded by the nucleic acid sequence SEQ ID NO: 8, wherein the medicament is for neutralizing swine-origin influenza A (H1N1) virus (S-OIV).

11. The medicament according to claim 10, wherein the monoclonal antibody is selected from the group consisting of whole immunoglobulins and immunoglobulin fragments, the immunoglobulin fragments comprising at least one heavy chain variable domain and at least one light chain variable domain.

12. The medicament according to claim 11, wherein said immunoglobulin fragments are selected from the group consisting of Fab fragments, Fab' fragments, $F(ab')_2$ fragments, Fv fragments, single chain antibodies (scFv).

13. The medicament according to claim 10, wherein the antibody is a human antibody.

14. A method for preparing a medicament according to claim 10, the method comprising:

preparing a monoclonal antibody suitable for neutralizing swine-origin influenza A (H1N1) virus (S-OIV) infections, wherein the antibody comprises one heavy chain variable domain consisting of the amino acid sequence SEQ ID NO:5 or fully encoded by the nucleic acid sequence SEQ ID NO:7 and one light chain variable domain consisting of the amino acid sequence SEQ ID NO:6 or being fully encoded by the nucleic acid sequence SEQ ID NO:8.

* * * * *

SEQUENCE LISTING

```
<160> NUMBER OF SEQ ID NOS: 15

<210> SEQ ID NO 1
<211> LENGTH: 122
<212> TYPE: PRT
<213> ORGANISM: Homo sapiens

<400> SEQUENCE: 1

Leu Glu Glu Ser Gly Gly Gly Val Val Gln Pro Gly Arg Ser Leu Arg
1               5                   10                  15

Leu Ser Cys Ala Ala Ser Gly Phe Pro Phe Ser Ser Tyr Gly Met His
            20                  25                  30

Trp Val Arg Gln Ala Pro Gly Lys Gly Leu Glu Trp Val Ala Gly Val
        35                  40                  45

Ser Tyr Asp Gly Ser Tyr Lys Tyr Tyr Ala Asp Ser Val Lys Gly Arg
    50                  55                  60

Phe Thr Ile Ser Arg Asp Ser Ser Lys Ser Thr Leu Tyr Leu Gln Met
65                  70                  75                  80

Asn Ser Leu Arg Pro Glu Asp Thr Ala Val Tyr Tyr Cys Ala Arg Pro
                85                  90                  95

Ser Ala Ile Phe Gly Ile Tyr Ile Ile Leu Asn Gly Leu Asp Val Trp
            100                 105                 110

Gly Gln Gly Thr Thr Val Thr Val Ser Ser
        115                 120

<210> SEQ ID NO 2
<211> LENGTH: 105
<212> TYPE: PRT
<213> ORGANISM: Homo sapiens
```

<400> SEQUENCE: 2

Glu Leu Thr Gln Ser Pro Ser Ser Val Ser Ala Ser Val Gly Asp Arg
1               5                   10                  15

Val Thr Ile Thr Cys Arg Ala Thr Gln Gly Ile Ser Ser Trp Leu Ala
            20                  25                  30

Trp Tyr Gln Gln Lys Pro Gly Lys Pro Pro Lys Leu Leu Ile Phe Gly
        35                  40                  45

Ala Ser Ser Leu Gln Ser Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80

Phe Ala Thr Tyr Phe Cys Gln Gln Ala His Ser Phe Pro Leu Thr Phe
                85                  90                  95

Gly Gly Gly Thr Lys Val Glu Ile Lys
            100                 105

<210> SEQ ID NO 3
<211> LENGTH: 366
<212> TYPE: DNA
<213> ORGANISM: Homo sapiens

<400> SEQUENCE: 3
ctcgaggagt ctgggggagg cgtggtccag cctggggaggt ccctgagact ctcctgtgca    60
gcctctggat tccccttcag tagttatggc atgcactggg tccgccaggc tccaggcaag   120
gggctggagt gggtggcagg tgtttcatat gatggaagtt ataaatacta tgcggactcc   180
gtcaagggcc gattcaccat ctccagagac agttccaaga gcactctata tctgcaaatg   240
aacagcctga cctgaggaa cacggctgtg tattactgtg cgagaccttc cgcgattttt   300
ggaatataca ttattctaaa cggtttggac gtctgggcc aagggaccac ggtcaccgtc   360
tcttca                                                              366

<210> SEQ ID NO 4
<211> LENGTH: 315
<212> TYPE: DNA
<213> ORGANISM: Homo sapiens

<400> SEQUENCE: 4
gagctcacgc agtctccatc ttccgtgtct gcatctgtag gagacagagt cactatcact    60
tgtcgggcga ctcagggtat tagtagttgg ttagcctggt atcagcagaa accagggaaa   120
ccacctaaac tcctgatttt tggtgcatct agtttgcaaa gtggggtccc atcaaggttc   180
agcggcagtg gatctgggac agatttcact ctcaccatca gcagtctaca gcctgaagat   240
tttgcaactt acttttgtca acaggctcac agtttcccgc tcactttcgg cggcgggacc   300
aaggtggaga tcaaa                                                    315

<210> SEQ ID NO 5
<211> LENGTH: 117
<212> TYPE: PRT
<213> ORGANISM: Homo sapiens

<400> SEQUENCE: 5

Leu Glu Ser Gly Gly Gly Leu Val Gln Pro Gly Gly Ser Leu Arg Leu
1               5                   10                  15

Ser Cys Ala Ala Ser Gly Ile Thr Phe Ser Ser Tyr Ala Met Ser Trp
            20                  25                  30

Val Arg Gln Ala Pro Gly Lys Gly Leu Glu Trp Val Ser Thr Val Asn

```
                35                  40                  45
Ser Gly Gly Ser Thr Tyr Tyr Gly Asp Ser Val Arg Gly Arg Phe
 50                  55                  60

Thr Ile Ser Arg Asp Asn Ser Lys Ser Thr Leu Tyr Leu Gln Leu Asn
 65                  70                  75                  80

Ser Leu Arg Ala Glu Asp Thr Ala Ile Tyr Tyr Cys Ala Lys Asp Lys
                 85                  90                  95

Gly Arg Pro Ile Phe Gly Leu Val Thr Pro Ser Tyr Tyr Met Asp Val
            100                 105                 110

Trp Gly Asn Gly Thr
        115

<210> SEQ ID NO 6
<211> LENGTH: 100
<212> TYPE: PRT
<213> ORGANISM: Homo sapiens

<400> SEQUENCE: 6

Glu Leu Thr Gln Ser Pro Ser Ser Leu Ser Ala Ser Val Gly Asp Ser
 1               5                  10                  15

Val Thr Ile Thr Cys Arg Thr Ser Glu Arg Ile Ser Thr Tyr Leu Asn
                 20                  25                  30

Trp Tyr Gln Gln Lys Pro Gly Lys Ala Pro Arg Leu Leu Val Ser Gly
                 35                  40                  45

Ala Ser Thr Leu Gln Gly Gly Val Pro Ser Arg Phe Ser Gly Ser Gly
 50                  55                  60

Ser Gly Thr Ala Phe Thr Leu Thr Ile Asn Ser Leu Gln Pro Glu Asp
 65                  70                  75                  80

Phe Ala Thr Tyr Tyr Cys Gln Gln Ser Tyr Ser Thr Pro Leu Thr Phe
                 85                  90                  95

Gly Gly Gly Thr
            100

<210> SEQ ID NO 7
<211> LENGTH: 351
<212> TYPE: DNA
<213> ORGANISM: Homo sapiens

<400> SEQUENCE: 7
ctcgagtctg ggggaggctt ggtacagcct ggggggtccc taagactctc ctgtgcagcc    60
tctggaatca catttagcag ctatgccatg agctgggtcc gccaggctcc agggaagggg   120
ctggagtggg tctcaactgt taacagtggt ggtggtagta catactacgg agactccgtg   180
aggggccggt tcaccatctc cagagacaac tccaagagca cgctgtacct gcaactgaac   240
agcctgagag ccgaggacac ggccatatat tactgtgcga agataaaggg tcgtccgatt   300
tttggactgg tcaccccatc atactacatg gacgtctggg gcaatgggac c           351

<210> SEQ ID NO 8
<211> LENGTH: 300
<212> TYPE: DNA
<213> ORGANISM: Homo sapiens

<400> SEQUENCE: 8
gagctcaccc agtctccatc ctccctgtct gcatctgtag gagacagcgt caccatcact    60
tgtcggacaa gtgagagaat tagcacctat ttaaattggt atcagcagaa accagggaaa   120 gccccctaggc tcctggtctc tggtgcatcc actttgcaag gtggggtccc atcaaggttc   180
```

-continued

```
agtggcagtg gatctgggac agctttcact cttaccatca acagtctgca gcctgaagat    240
tttgcaactt actactgtca acagagttac agtaccccac tcactttcgg cggagggacc    300
```

<210> SEQ ID NO 9
<211> LENGTH: 859
<212> TYPE: DNA
<213> ORGANISM: Influenza A virus

<400> SEQUENCE: 9

```
gtattatcat tcagatacac cagtccacga ttgcaataca acttgtcaga cacccaaggg     60
tgctataaac accagcctcc catttcagaa tatacatccg atcacaattg aaaatgtcc    120 aaaatatgta aaaagcacaa aattgagact ggccacagga ttgaggaatg tcccgtctat    180
tcaatctaga ggcctatttg gggccattgc cggtttcatt gaaggggggt ggacagggat    240
ggtagatgga tggtttattt gtctcaggga gcaaaagcag gggtcaggat atgcagccga    300
cctgaagagc acacagaatg ccattgacga gattactaac aaagtaaatt ctgttattga    360
aaagatgaat acacagttca cagcagtagg taaagagttc aaccacctgg aaaaaagaat    420
agagaattta aataaaaaag ttgatgatgg tttcctggac atttggactt acaatgccga    480
actgttggtt ctattggaaa atgaaagaac tttggactac cacgattcaa atgtgaagaa    540
cttatatgaa aaggtaagaa accagttaaa aaacaatgcc aaggaaattg aaacggctg    600 ctttgaattt taccacaaat gcgataacac gtgcatggaa agtgtcaaaa atgggactta    660
tgactaccca aaatactcag aggaagcaaa attaaacaga gaagaaatag atggggtaaa    720
gctggaatca acaaggattt accagatttt ggcgatctat tcaactgtcg ccagttcatt    780
ggtactggta gtctccctgg gggcaatcag tttctggatg tgctctaatg ggtctctaca    840
gtgtagaata tgtatttaa                                                 859
```

<210> SEQ ID NO 10
<211> LENGTH: 286
<212> TYPE: PRT
<213> ORGANISM: Influenza A virus
<220> FEATURE:
<221> NAME/KEY: misc_feature
<222> LOCATION: (4)..(4)
<223> OTHER INFORMATION: Xaa can be any naturally occurring amino acid

<400> SEQUENCE: 10

```
Val Leu Ser Xaa Ser Asp Thr Pro Val His Asp Cys Asn Thr Thr Cys
1               5                   10                  15

Gln Thr Pro Lys Gly Ala Ile Asn Thr Ser Leu Pro Phe Gln Asn Ile
            20                  25                  30

His Pro Ile Thr Ile Gly Lys Cys Pro Lys Tyr Val Lys Ser Thr Lys
        35                  40                  45

Leu Arg Leu Ala Thr Gly Leu Arg Asn Val Pro Ser Ile Gln Ser Arg
    50                  55                  60

Gly Leu Phe Gly Ala Ile Ala Gly Phe Ile Glu Gly Gly Trp Thr Gly
65                  70                  75                  80

Met Val Asp Gly Trp Phe Ile Cys Leu Arg Glu Gln Lys Gln Gly Ser
                85                  90                  95

Gly Tyr Ala Ala Asp Leu Lys Ser Thr Gln Asn Ala Ile Asp Glu Ile
            100                 105                 110

Thr Asn Lys Val Asn Ser Val Ile Glu Lys Met Asn Thr Gln Phe Thr
        115                 120                 125

Ala Val Gly Lys Glu Phe Asn His Leu Glu Lys Arg Ile Glu Asn Leu
    130                 135                 140
```

Asn Lys Lys Val Asp Asp Gly Phe Leu Asp Ile Trp Thr Tyr Asn Ala
145                 150                 155                 160

Glu Leu Leu Val Leu Leu Glu Asn Glu Arg Thr Leu Asp Tyr His Asp
            165                 170                 175

Ser Asn Val Lys Asn Leu Tyr Glu Lys Val Arg Asn Gln Leu Lys Asn
            180                 185                 190

Asn Ala Lys Glu Ile Gly Asn Gly Cys Phe Glu Phe Tyr His Lys Cys
            195                 200                 205

Asp Asn Thr Cys Met Glu Ser Val Lys Asn Gly Thr Tyr Asp Tyr Pro
    210                 215                 220

Lys Tyr Ser Glu Glu Ala Lys Leu Asn Arg Glu Glu Ile Asp Gly Val
225                 230                 235                 240

Lys Leu Glu Ser Thr Arg Ile Tyr Gln Ile Leu Ala Ile Tyr Ser Thr
            245                 250                 255

Val Ala Ser Ser Leu Val Leu Val Val Ser Leu Gly Ala Ile Ser Phe
            260                 265                 270

Trp Met Cys Ser Asn Gly Ser Leu Gln Cys Arg Ile Cys Ile
            275                 280                 285

```
<210> SEQ ID NO 11
<211> LENGTH: 34
<212> TYPE: DNA
<213> ORGANISM: Artificial
<220> FEATURE:
<223> OTHER INFORMATION: Primer Bm-NS-890-Rev

<400> SEQUENCE: 11
atatcgtctc gtattagtag aaacaagggt gttt                        34

<210> SEQ ID NO 12
<211> LENGTH: 28
<212> TYPE: DNA
<213> ORGANISM: Artificial
<220> FEATURE:
<223> OTHER INFORMATION: Primer Bm-HA-1-Fw

<400> SEQUENCE: 12
tattcgtctc agggagcaaa agcagggg                              28

<210> SEQ ID NO 13
<211> LENGTH: 20
<212> TYPE: DNA
<213> ORGANISM: Artificial
<220> FEATURE:
<223> OTHER INFORMATION: Primer H1-F1

<400> SEQUENCE: 13
cttaggaaac ccagaatgcg                                       20

<210> SEQ ID NO 14
<211> LENGTH: 20
<212> TYPE: DNA
<213> ORGANISM: Artificial
<220> FEATURE:
<223> OTHER INFORMATION: Primer H1-F2

<400> SEQUENCE: 14
tactggacct tgctagaacc                                       20

<210> SEQ ID NO 15
<211> LENGTH: 20
<212> TYPE: DNA
```

-continued

```
<213> ORGANISM: Artificial
<220> FEATURE:
<223> OTHER INFORMATION: Primer H1-F3

<400> SEQUENCE: 15
ggtctatttg gagccattgc                                                20
```